(12) United States Patent
Portal et al.

(10) Patent No.: US 10,071,046 B2
(45) Date of Patent: Sep. 11, 2018

(54) DISPERSION OF POLYMER PARTICLES IN A NON-AQUEOUS MEDIUM AND COSMETIC USE THEREOF

(71) Applicant: L'OREAL, Paris (FR)

(72) Inventors: Julien Portal, Les Pavillions sous Bois (FR); Xavier Schultze, Les Pavillons sous Bois (FR); Simon Taupin, Antony (FR); Marco Vicic, Bry sur Marne (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/105,293

(22) PCT Filed: Dec. 16, 2014

(86) PCT No.: PCT/EP2014/078003
§ 371 (c)(1),
(2) Date: Jun. 16, 2016

(87) PCT Pub. No.: WO2015/091513
PCT Pub. Date: Jun. 25, 2015

(65) Prior Publication Data
US 2016/0317423 A1    Nov. 3, 2016

(30) Foreign Application Priority Data

Dec. 17, 2013 (FR) .................................. 13 62795

(51) Int. Cl.
| | |
|---|---|
| *A61K 8/81* | (2006.01) |
| *A61K 8/31* | (2006.01) |
| *A61K 8/04* | (2006.01) |
| *A61K 8/02* | (2006.01) |
| *A61K 8/37* | (2006.01) |
| *A61Q 1/04* | (2006.01) |
| *A61Q 1/10* | (2006.01) |
| *A61K 8/19* | (2006.01) |
| *A61K 8/46* | (2006.01) |
| *C08F 265/06* | (2006.01) |
| *C08L 33/08* | (2006.01) |
| *A61Q 1/02* | (2006.01) |
| *A61K 8/58* | (2006.01) |
| *A61Q 1/06* | (2006.01) |

(52) U.S. Cl.
CPC .......... *A61K 8/8152* (2013.01); *A61K 8/0216* (2013.01); *A61K 8/04* (2013.01); *A61K 8/044* (2013.01); *A61K 8/19* (2013.01); *A61K 8/31* (2013.01); *A61K 8/37* (2013.01); *A61K 8/466* (2013.01); *A61K 8/585* (2013.01); *A61Q 1/02* (2013.01); *A61Q 1/04* (2013.01); *A61Q 1/10* (2013.01); *C08F 265/06* (2013.01); *C08L 33/08* (2013.01); *A61K 2800/43* (2013.01); *A61K 2800/52* (2013.01); *A61K 2800/594* (2013.01); *A61Q 1/06* (2013.01)

(58) Field of Classification Search
CPC ................ A61K 8/044; A61K 2800/43; A61K 2800/52; A61K 2800/594; A61Q 1/02; A61Q 1/04
See application file for complete search history.

(56) References Cited

U.S. PATENT DOCUMENTS

| | | | | |
|---|---|---|---|---|
| 5,616,598 | A * | 4/1997 | Lion | ...................... A61K 8/044 424/63 |
| 5,851,517 | A * | 12/1998 | Mougin | ................. A61K 8/044 424/401 |
| 2011/0243864 | A1* | 10/2011 | Farcet | ...................... A61K 8/04 424/61 |

FOREIGN PATENT DOCUMENTS

| | | |
|---|---|---|
| EP | 0749746 A1 | 12/1996 |
| EP | 0749747 A1 | 12/1996 |
| FR | 2785530 A1 | 5/2000 |
| FR | 2937645 A1 | 4/2010 |
| FR | 2972630 A1 | 9/2012 |
| FR | 2972631 A1 | 9/2012 |

\* cited by examiner

*Primary Examiner* — Jianfeng Song
(74) *Attorney, Agent, or Firm* — Polsinelli PC

(57) ABSTRACT

Provided is a dispersion of polymer particles, wherein the polymer is surface-stabilized with a stabilizer in a non-aqueous medium containing at least one hydrocarbon-based oil. The polymer of the particles is a C1-C4 alkyl (meth) acrylate polymer; and the stabilizer is an isobornyl (meth) acrylate polymer. Also provided is a composition that comprises the dispersion of polymer particles. The dispersion can be used as a cosmetic for caring for and making up of keratin materials.

18 Claims, No Drawings

DISPERSION OF POLYMER PARTICLES IN A NON-AQUEOUS MEDIUM AND COSMETIC USE THEREOF

CROSS REFERENCE TO RELATED APPLICATIONS

This application is a National Phase filing under 35 U.S.C. § 371 of PCT/EP2014/078003 filed on Dec. 16, 2014; and this application claims priority to Application No. 1362795 filed in France on Dec. 17, 2013, under 35 U.S.C. § 119. The entire contents of each application are hereby incorporated by reference.

The present invention relates to a dispersion of polymer particles dispersed in a non-aqueous medium, and also to a cosmetic composition comprising such a dispersion.

It is known practice to use in cosmetics dispersions of polymer particles of nano-metric size, in organic media such as hydrocarbon-based oils, for instance hydrocarbons. Polymers are especially used as film-forming agents in makeup products such as mascaras, eyeliners, eyeshadows or lipsticks.

Document EP-A-749 747 describes in the examples dispersions in hydrocarbon-based oils (liquid paraffin, isododecane) of acrylic polymers stabilized with polystyrene/copoly (ethylene-propylene) diblock copolymers. However, when the solids (polymer+stabilizer) content exceeds 25% by weight, the dispersion then becomes too viscous, thus giving rise to formulation difficulties in cosmetic products on account of a large change in the viscosity of the final composition of these products. In addition, the film obtained after application of the dispersion to the skin is slightly glossy.

Document WO-A-2010/046 229 describes dispersions in isododecane of acrylic polymers stabilized with block and especially triblock stabilizing polymers of acrylic monomers. In the examples, according to Example 1A, the stabilizing polymer is prepared by reversible chain-transfer controlled radical polymerization. This polymerization method is difficult to perform on an industrial scale since it requires a large number of intermediate purification steps to obtain the final polymer dispersion.

There is thus a need for a stable dispersion of acrylic polymer stabilized in a non-aqueous medium comprising a hydrocarbon-based oil, which is easy to manufacture industrially, and which makes it possible to obtain a film that has good cosmetic properties, especially good gloss.

The Applicant has discovered that novel dispersions of C1-C4 alkyl (meth)acrylate polymer particles stabilized with particular stabilizers based on isobornyl (meth)acrylate polymer in a hydrocarbon-based oil have good stability, especially after storage for seven days at room temperature (25° C.), are easy to manufacture industrially without using a large number of synthetic steps and also make it possible to obtain a film after application to a support which has good cosmetic properties, in particular good gloss, good resistance to oils, and which is non-tacky.

One subject of the present invention is thus a dispersion of particles of at least one polymer that is surface-stabilized with a stabilizer in a non-aqueous medium containing at least one hydrocarbon-based oil, the polymer of the particles being a C1-C4 alkyl (meth)acrylate polymer; the stabilizer being an isobornyl (meth)acrylate polymer chosen from isobornyl (meth)acrylate homopolymer and statistical copolymers of isobornyl (meth)acrylate and of C1-C4 alkyl (meth)acrylate present in an isobornyl (meth)acrylate/C1-C4 alkyl (meth)acrylate weight ratio of greater than 4. For these statistical stabilizing copolymers, the defined weight ratio makes it possible to obtain a polymer dispersion that is stable, especially after storage for seven days at room temperature (25° C.).

Another subject of the invention is a composition comprising, in a physiologically acceptable medium, a polymer particle dispersion as defined previously.

A subject of the invention is also a process for the non-therapeutic cosmetic treatment of keratin materials, comprising the application to the keratin materials of a composition as defined previously. The treatment process is in particular a process for caring for or making up keratin materials.

The dispersions according to the invention thus consist of particles, which are generally spherical, of at least one surface-stabilized polymer, in a non-aqueous medium.

The polymer of the particles is a C1-C4 alkyl (meth)acrylate polymer.

The C1-C4 alkyl (meth)acrylate monomers may be chosen from methyl (meth)acrylate, ethyl (meth)acrylate, n-propyl (meth)acrylate, isopropyl (meth)acrylate, n-butyl (meth)acrylate and tert-butyl (meth)acrylate.

A C1-C4 alkyl acrylate monomer is advantageously used. Preferentially, the polymer of the particles is a methyl acrylate and/or ethyl acrylate polymer.

The polymer of the particles may also comprise an ethylenically unsaturated acid monomer or the anhydride thereof, chosen especially from ethylenically unsaturated acid monomers comprising at least one carboxylic, phosphoric or sulfonic acid function, such as crotonic acid, itaconic acid, fumaric acid, maleic acid, maleic anhydride, styrenesulfonic acid, vinylbenzoic acid, vinylphosphoric acid, acrylic acid, methacrylic acid, acrylamidopropanesulfonic acid or acrylamidoglycolic acid, and salts thereof.

Preferably, the ethylenically unsaturated acid monomer is chosen from (meth)acrylic acid, maleic acid and maleic anhydride.

The salts may be chosen from salts of alkali metals, for example sodium or potassium; salts of alkaline-earth metals, for example calcium, magnesium or strontium; metal salts, for example zinc, aluminium, manganese or copper; ammonium salts of formula $NH_4^+$; quaternary ammonium salts; salts of organic amines, for instance salts of methylamine, dimethylamine, trimethylamine, triethylamine, ethylamine, 2-hydroxyethylamine, bis(2-hydroxyethyl)amine or tris(2-hydroxyethyl)amine; lysine or arginine salts.

The polymer of the particles may thus comprise or consist essentially of 80% to 100% by weight of C1-C4 alkyl (meth)acrylate and of 0 to 20% by weight of ethylenically unsaturated acid monomer, relative to the total weight of the polymer. According to a first embodiment of the invention, the polymer consists essentially of a polymer of one or more C1-C4 alkyl (meth)acrylate monomers.

According to a second embodiment of the invention, the polymer consists essentially of a copolymer of C1-C4 (meth)acrylate and of (meth)acrylic acid or maleic anhydride.

The polymer of the particles may be chosen from:
methyl acrylate homopolymers
ethyl acrylate homopolymers
methyl acrylate/ethyl acrylate copolymers
methyl acrylate/ethyl acrylate/acrylic acid copolymers
methyl acrylate/ethyl acrylate/maleic anhydride copolymers
methyl acrylate/acrylic acid copolymers
ethyl acrylate/acrylic acid copolymers
methyl acrylate/maleic anhydride copolymers ethyl acrylate/maleic anhydride copolymers.

Advantageously, the polymer of the particles is a non-crosslinked polymer.

The polymer of the particles of the dispersion preferably has a number-average molecular weight ranging from 2000 to 10 000 000 and preferably ranging from 150 000 to 500 000.

The polymer of the particles may be present in the dispersion in a content ranging from 21% to 58.5% by weight and preferably ranging from 36% to 42% by weight, relative to the total weight of the dispersion.

The stabilizer is an isobornyl (meth)acrylate polymer chosen from isobornyl (meth)acrylate homopolymer and statistical copolymers of isobornyl (meth)acrylate and of C1-C4 alkyl (meth)acrylate present in an isobornyl (meth)acrylate/C1-C4 alkyl (meth)acrylate weight ratio of greater than 4, preferably greater than 4,5, more preferably greater or equal to 5. Advantageously, the said weight ratio ranges from 4.5 to 19, and preferably from 5 to 19, and more preferably from 5 to 12.

Advantageously, the stabilizer is chosen from:
isobornyl acrylate homopolymers
statistical copolymers of isobornyl acrylate/methyl acrylate
statistical copolymers of isobornyl acrylate/methyl acrylate/ethyl acrylate
statistical copolymers of isobornyl methacrylate/methyl acrylate
in the weight ratio described previously.

The stabilizing polymer preferably has a number-average molecular weight ranging from 10 000 to 400 000 and preferably ranging from 20 000 to 200 000.

The stabilizer is in contact with the surface of the polymer particles and thus makes it possible to stabilize these particles at the surface in order to keep these particles in dispersion in the non-aqueous medium of the dispersion. The stabilizer is a compound distinct form the polymer of the particles.

Advantageously, the combination of the stabilizer+polymer of the particles present in the dispersion comprises from 10% to 50% by weight of polymerized isobornyl (meth)acrylate and from 50% to 90% by weight of polymerized C1-C4 alkyl (meth)acrylate, relative to the total weight of the combination of the stabilizer+polymer of the particles.

Preferentially, the combination of the stabilizer+polymer of the particles present in the dispersion comprises from 15% to 30% by weight of polymerized isobornyl (meth)acrylate and from 70% to 85% by weight of polymerized C1-C4 alkyl (meth)acrylate, relative to the total weight of the combination of the stabilizer+polymer of the particles.

The oily medium of the polymer dispersion comprises a hydrocarbon-based oil. The hydrocarbon-based oil is an oil that is liquid at room temperature (25° C.).

The term "hydrocarbon-based oil" means an oil formed essentially from, or even consisting of, carbon and hydrogen atoms, and optionally oxygen and nitrogen atoms, and not containing any silicon or fluorine atoms. It may contain alcohol, ester, ether, carboxylic acid, amine and/or amide groups.

The hydrocarbon-based oil may be chosen from:
hydrocarbon-based oils containing from 8 to 16 carbon atoms, and especially:
branched $C_8$-$C_{14}$ alkanes, for instance $C_8$-$C_{14}$ isoalkanes of petroleum origin (also known as isoparaffins), for instance isododecane (also known as 2,2,4,4,6-pentamethylheptane), isodecane, isohexadecane and, for example, the oils sold under the trade name Isopar or Permethyl,
linear alkanes, for instance n-dodecane (C12) and n-tetradecane (C14) sold by Sasol under the respective references Parafol 12-97 and Parafol 14-97, and also mixtures thereof, the undecane-tridecane mixture, the mixtures of n-undecane (C11) and of n-tridecane (C13) obtained in Examples 1 and 2 of patent application WO 2008/155 059 from the company Cognis, and mixtures thereof,
short-chain esters (containing from 3 to 8 carbon atoms in total) such as ethyl acetate, methyl acetate, propyl acetate or n-butyl acetate,
hydrocarbon-based oils of plant origin such as triglycerides consisting of fatty acid esters of glycerol, the fatty acids of which may have chain lengths varying from $C_4$ to $C_{24}$, these chains possibly being linear or branched, and saturated or unsaturated; these oils are especially heptanoic or octanoic acid triglycerides, or alternatively wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion-flower oil and musk rose oil; shea butter; or else caprylic/capric acid triglycerides, for instance those sold by the company Stéarineries Dubois or those sold under the names Miglyol 810®, 812® and 818® by the company Dynamit Nobel,
synthetic ethers containing from 10 to 40 carbon atoms;
linear or branched hydrocarbons of mineral or synthetic origin, such as petroleum jelly, polydecenes, hydrogenated polyisobutene such as Parleam®, squalane and liquid paraffins, and mixtures thereof,
synthetic esters such as oils of formula $R_1COOR_2$ in which $R_1$ represents a linear or branched fatty acid residue containing from 1 to 40 carbon atoms and $R_2$ represents an, in particular, branched hydrocarbon-based chain containing from 1 to 40 carbon atoms, on condition that $R_1+R_2 \geq 10$, for instance purcellin oil (cetostearyl octanoate), isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, alkyl or polyalkyl heptanoates, octanoates, decanoates or ricinoleates such as propylene glycol dioctanoate; hydroxylated esters such as isostearyl lactate, diisostearyl malate and 2-octyldodecyl lactate; polyol esters and pentaerythritol esters,
fatty alcohols that are liquid at room temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol.

Advantageously, the hydrocarbon-based oil is apolar (thus formed solely from carbon and hydrogen atoms).

The hydrocarbon-based oil is preferably chosen from hydrocarbon-based oils containing from 8 to 16 carbon atoms, preferably from 8 to 14 carbon atoms, in particular the apolar oils described previously.

Preferentially, the hydrocarbon-based oil is isododecane.

The polymer particles of the dispersion preferably have an average size, especially a number-average size, ranging from 50 to 500 nm, especially ranging from 75 to 400 nm and better still ranging from 100 to 250 nm.

In general, the dispersion according to the invention may be prepared in the following manner, which is given as an example.

The polymerization may be performed in dispersion, i.e. by precipitation of the polymer during formation, with protection of the formed particles with a stabilizer.

In a first step, the stabilizing polymer is prepared by mixing the constituent monomer(s) of the stabilizing polymer, with a radical initiator, in a solvent known as the synthesis solvent, and by polymerizing these monomers. In a second step, the constituent monomer(s) of the polymer of the particles are added to the stabilizing polymer formed and polymerization of these added monomers is performed in the presence of the radical initiator.

When the non-aqueous medium is a non-volatile hydrocarbon-based oil, the polymerization may be performed in an apolar organic solvent (synthesis solvent), followed by adding the non-volatile hydrocarbon-based oil (which should be miscible with the said synthesis solvent) and selectively distilling off the synthesis solvent.

A synthesis solvent which is such that the monomers of the stabilizing polymer and the free-radical initiator are soluble therein, and the polymer particles obtained are insoluble therein, so that they precipitate therein during their formation, is thus chosen.

In particular, the synthesis solvent may be chosen from alkanes such as heptane or cyclohexane.

When the non-aqueous medium is a volatile hydrocarbon-based oil, the polymerization may be performed directly in the said oil, which thus also acts as synthesis solvent. The monomers should also be soluble therein, as should the free-radical initiator, and the polymer of the particles obtained should be insoluble therein.

The monomers are preferably present in the synthesis solvent, before polymerization, in a proportion of 5-20% by weight. The total amount of monomers may be present in the solvent before the start of the reaction, or part of the monomers may be added gradually as the polymerization reaction proceeds.

The free-radical initiator may especially be azobisisobutyronitrile or tert-butyl peroxy-2-ethylhexanoate.

The polymerization may be performed at a temperature ranging from 70 to 110° C.

The polymer particles are surface-stabilized, when they are formed during the polymerization, by means of the stabilizer.

The stabilization may be performed by any known means, and in particular by direct addition of the stabilizer, during the polymerization.

The stabilizer is preferably also present in the mixture before polymerization of the monomers of the polymer of the particles. However, it is also possible to add it continuously, especially when the monomers of the polymer of the particles are also added continuously.

From 10% to 30% by weight and preferably from 15% to 25% by weight of stabilizer may be used relative to the total weight of monomers used (stabilizer+polymer of the particles).

The polymer particle dispersion advantageously comprises from 30% to 65% by weight and preferably from 40% to 60% by weight of solids, relative to the total weight of the dispersion.

Advantageously, the oily dispersion may comprise a plasticizer chosen from tri-n-butyl citrate, tripropylene glycol monomethyl ether (INCI name: PPG-3 methyl ether) and trimethyl pentaphenyl trisiloxane (sold under the name Dow Corning PH-1555 HRI Cosmetic Fluid by the company Dow Corning). These plasticizers make it possible to improve the mechanical strength of the polymer film.

The plasticizer may be present in the oily dispersion in an amount ranging from 5% to 50% by weight, relative to the total weight of the polymer of the particles.

The polymer dispersion obtained according to the invention may be used in a composition comprising a physiologically acceptable medium, in particular in a cosmetic composition.

The term "physiologically acceptable medium" is intended to mean a medium that is compatible with human keratin materials, for instance the skin, the lips, the nails, the eyelashes, the eyebrows or the hair.

The term "cosmetic composition" is understood to mean a composition that is compatible with keratin materials, which has a pleasant colour, odour and feel and which does not cause unacceptable discomfort (stinging, tautness or redness) liable to discourage the consumer from using it.

The term "keratin materials" is understood to mean the skin (body, face, contour of the eyes, scalp), head hair, eyelashes, eyebrows, bodily hairs, nails or lips.

The composition according to the invention may comprise a cosmetic additive chosen from water, fragrances, preserving agents, fillers, dyestuffs, UV-screening agents, oils, waxes, surfactants, moisturizers, vitamins, ceramides, antioxidants, free-radical scavengers, polymers and thickeners.

The composition according to the invention may comprise the polymer of the dispersion in a content ranging from 1% to 50% by weight and preferably ranging from 10% to 45% by weight relative to the total weight of the composition.

Advantageously, the composition according to the invention is a makeup composition, in particular a lip makeup composition, a mascara, an eyeliner, an eyeshadow or a foundation.

According to one embodiment, the composition according to the invention is an anhydrous composition. The term "anhydrous composition" means a composition containing less than 2% by weight of water, or even less than 0.5% of water, and is especially free of water. Where appropriate, such small amounts of water may especially be introduced by ingredients of the composition that may contain residual amounts thereof.

The invention is illustrated in greater detail in the examples that follow.

Evaluation of the Cosmetic Properties of the Oily Dispersions:

The oily dispersion to be evaluated was placed on a contrast card (for example that sold under the reference Byko-charts by the company Byk-Gardner) and the film deposited was dried for 24 hours at room temperature (25° C.). The dry film has a thickness of about 50 μm.

The gloss of the film was measured using a glossmeter (three angles Refo 3/Refo 3D from Labomat) at an angle of 20°.

The resistance of the film to the fatty substance was determined by depositing on the dry film three drops of olive oil onto the black part of the contrast card. The drops were left in contact with the dry film for 10 minutes, 30 minutes and 60 minutes, respectively, and the oil drop was then wiped and the appearance of the area of the film that was in contact with the oil was observed. If the film was damaged by the oil drop, the polymer film is considered as not being resistant to olive oil.

The tacky aspect of the polymer film was evaluated by touching the dry film with a finger.

All the percentages of reagents described in the examples are weight percentages.

EXAMPLE 1

In a first step, 1300 g of isododecane, 337 g of isobornyl acrylate, 28 g of methyl acrylate and 3.64 g of tert-butyl peroxy-2-ethylhexanoate (Trigonox 21S from Akzo) were placed in a reactor. The isobornyl acrylate/methyl acrylate mass ratio is 92/8. The mixture was heated at 90° C. under argon with stirring.

After 2 hours of reaction, 1430 g of isododecane were added to the reactor feed-stock and the mixture was heated to 90° C.

In a second step, a mixture of 1376 g of methyl acrylate, 1376 g of isododecane and 13.75 g of Trigonox 21 S were run in over 2 hours 30 minutes, and the mixture was left to react for 7 hours. 3.3 liters of isododecane were then added and part of the isododecane was evaporated off to obtain a solids content of 50% by weight.

A dispersion of methyl acrylate particles stabilized with a statistical copolymer stabilizer containing 92% isobornyl acrylate and 8% methyl acrylate in isododecane was obtained.

The oily dispersion contains in total (stabilizer+particles) 80% methyl acrylate and 20% isobornyl acrylate.

The polymer particles of the dispersion have a number-average size of about 160 nm.

The dispersion is stable after storage for 7 days at room temperature (25° C.).

The film obtained with the oily dispersion has the following properties:

| Gloss at 20° | Resistance to fatty substances | Tacky |
|---|---|---|
| 72 | Resistant to fatty substances | Non-tacky |

EXAMPLE 2

A dispersion of polymer in isododecane was prepared according to the preparation method of Example 1, using:

Step 1: 275.5 g of isobornyl acrylate, 11.6 g of methyl acrylate, 11.6 g of ethyl acrylate, 2.99 g of Trigonox 21, 750 g of isododecane; followed by addition, after reaction, of 750 g of isododecane.

Step 2: 539.5 g of methyl acrylate, 539.5 g of ethyl acrylate, 10.8 g of Trigonox 21S, 1079 g of isododecane. After reaction, addition of 2 liters of isododecane and evaporation to obtain a solids content of 35% by weight.

A dispersion in isododecane of methyl acrylate/ethyl acrylate (50/50) copolymer particles stabilized with an isobornyl acrylate/methyl acrylate/ethyl acrylate (92/4/4) statistical copolymer stabilizer was obtained.

The oily dispersion contains in total (stabilizer+particles) 40% methyl acrylate, 40% ethyl acrylate and 20% isobornyl acrylate.

The dispersion is stable after storage for 7 days at room temperature (25° C.).

The film obtained with the oily dispersion has the following properties:

| Gloss at 20° | Resistance to fatty substances | Tacky |
|---|---|---|
| 71 | Resistant to fatty substances | Non-tacky |

EXAMPLE 3

A dispersion of polymer in isododecane was prepared according to the preparation method of Example 1, using:

Step 1: 315.2 g of isobornyl acrylate, 12.5 g of methyl acrylate, 12.5 g of ethyl acrylate, 3.4 g of Trigonox 21, 540 g of isododecane, 360 g of ethyl acetate; followed by addition, after reaction, of 540 g of isododecane and 360 g of ethyl acetate.

Step 2: 303 g of methyl acrylate, 776 g of ethyl acrylate, 157 g of acrylic acid, 11 g of Trigonox 21S, 741.6 g of isododecane and 494.4 g of ethyl acetate. After reaction, addition of 3 liters of an isododecane/ethyl acetate mixture (60/40 weight/weight) and total evaporation of the ethyl acetate and partial evaporation of the isododecane to obtain a solids content of 44% by weight.

A dispersion in isododecane of methyl acrylate/ethyl acrylate/acrylic acid (24.5/62.8/12.7) copolymer particles stabilized with an isobornyl acrylate/methyl acrylate/ethyl acrylate (92/4/4) statistical copolymer stabilizer was obtained.

The oily dispersion contains in total (stabilizer+particles) 10% acrylic acid, 20% methyl acrylate, 50% ethyl acrylate and 20% isobornyl acrylate.

The dispersion is stable after storage for 7 days at room temperature (25° C.).

The film obtained with the oily dispersion has the following properties:

| Gloss at 20° | Resistance to fatty substances | Tacky |
|---|---|---|
| 74 | Resistant to fatty substances | Non-tacky |

EXAMPLE 4

A dispersion of polymer in isododecane was prepared according to the preparation method of Example 1, using:

Step 1: 315.2 g of isobornyl acrylate, 12.5 g of methyl acrylate, 12.5 g of ethyl acrylate, 3.4 g of Trigonox 21, 540 g of isododecane, 360 g of ethyl acetate; followed by addition, after reaction, of 540 g of isododecane and 360 g of ethyl acetate.

Step 2: 145 g of methyl acrylate, 934 g of ethyl acrylate, 157 g of acrylic acid, 12.36 g of Trigonox 21S, 741.6 g of isododecane and 494.4 g of ethyl acetate. After reaction, addition of 3 liters of an isododecane/ethyl acetate mixture (60/40 weight/weight) and total evaporation of the ethyl acetate and partial evaporation of the isododecane to obtain a solids content of 44% by weight.

A dispersion in isododecane of methyl acrylate/ethyl acrylate/acrylic acid (11.7/75.6/12.7) copolymer particles stabilized with an isobornyl acrylate/methyl acrylate/ethyl acrylate (92/4/4) statistical copolymer stabilizer was obtained.

The oily dispersion contains in total (stabilizer+particles) 10% acrylic acid, 10% methyl acrylate, 60% ethyl acrylate and 20% isobornyl acrylate.

The dispersion is stable after storage for 7 days at room temperature (25° C.).

The film obtained with the oily dispersion has the following properties:

| Gloss at 20° | Resistance to fatty substances | Tacky |
|---|---|---|
| 73 | Resistant to fatty substances | Non-tacky |

EXAMPLE 5

A dispersion of polymer in isododecane was prepared according to the preparation method of Example 1, using:

Step 1: 48 g of isobornyl acrylate, 2 g of methyl acrylate, 2 g of ethyl acrylate, 0.52 g of Trigonox 21, 57.6 g of isododecane, 38.4 g of ethyl acetate; followed by addition, after reaction, of 540 g of isododecane and 360 g of ethyl acetate.

Step 2: 98 g of methyl acrylate, 73 g of ethyl acrylate, 25 g of maleic anhydride, 1.96 g of Trigonox 21S, 50.4 g of isododecane and 33.60 g of ethyl acetate. After reaction, addition of 1 liter of an isododecane/ethyl acetate mixture (60/40 weight/weight) and total evaporation of the ethyl acetate and partial evaporation of the isododecane to obtain a solids content of 46.2% by weight.

A dispersion in isododecane of methyl acrylate/ethyl acrylate/maleic anhydride (50/37.2/12.8) copolymer particles stabilized with an isobornyl acrylate/methyl acrylate/ethyl acrylate (92/4/4) statistical copolymer stabilizer was obtained.

The oily dispersion contains in total (stabilizer+particles) 10% maleic anhydride, 30% methyl acrylate, 40% ethyl acrylate and 20% isobornyl acrylate.

The dispersion is stable after storage for 7 days at room temperature (25° C.).

The film obtained with the oily dispersion has the following properties:

| Gloss at 20° | Resistance to fatty substances | Tacky |
|---|---|---|
| 70 | Resistant to fatty substances | Non-tacky |

EXAMPLE 6

A dispersion of polymer in isododecane was prepared according to the preparation method of Example 1, using:

Step 1: 48.5 g of isobornyl methacrylate, 4 g of methyl acrylate, 0.52 g Trigonox 21, 115 g of isododecane; followed by addition, after reaction, of 80 g of isododecane.

Step 2: 190 g of methyl acrylate, 1.9 g of Trigonox 21S, 190 g of isododecane. After reaction, addition of 1 liter of isododecane and partial evaporation of the isododecane to obtain a solids content of 48% by weight.

A dispersion in isododecane of methyl acrylate polymer particles stabilized with an isobornyl methacrylate/methyl acrylate (92/8) statistical copolymer stabilizer was obtained.

The oily dispersion contains in total (stabilizer+particles) 80% methyl acrylate and 20% isobornyl methacrylate.

The dispersion is stable after storage for 7 days at room temperature (25° C.).

The film obtained with the oily dispersion has the following properties:

| Gloss at 20° | Resistance to fatty substances | Tacky |
|---|---|---|
| 69 | Resistant to fatty substances | Non-tacky |

EXAMPLES 7 AND 8 (INVENTION) AND 9 AND 10 (OUTSIDE THE INVENTION)

Several oily dispersions of polymethyl acrylate stabilized with a stabilizer containing isobornyl acrylate and optionally methyl acrylate were prepared, according to the procedure of Example 1, by varying the mass ratio of isobornyl acrylate and methyl acrylate and observing the stability of the dispersion obtained as a function of the chemical constitution of the stabilizer.

All the dispersions comprise in total (stabilizer+particles) 80% methyl acrylate and 20% isobornyl acrylate.

EXAMPLE 7

Step 1: 50 g of isobornyl acrylate, 0.5 g Trigonox 21, 96 g of isododecane; followed by addition, after reaction, of 80 g of isododecane.

Step 2: 200 g of methyl acrylate, 2 g of Trigonox 21S, 200 g of isododecane. After reaction, addition of 80 g of isododecane and evaporation to obtain a solids content of 31% by weight.

A dispersion in isododecane of polymethyl acrylate particles stabilized with a poly-isobornyl acrylate stabilizer was obtained.

EXAMPLE 8

Step 1: 48.5 g of isobornyl acrylate, 8.5 g of methyl acrylate, 0.57 g Trigonox 21, 115 g of isododecane; followed by addition, after reaction, of 75 g of isododecane.

Step 2: 185.5 g of methyl acrylate, 1.85 g of Trigonox 21S, 185.5 g of isododecane. After reaction, addition of 75 g of isododecane and evaporation to obtain a solids content of 31% by weight.

A dispersion in isododecane of polymethyl acrylate particles stabilized with an isobornyl acrylate/methyl acrylate (85/15) statistical copolymer stabilizer was obtained.

EXAMPLE 9 (OUTSIDE THE INVENTION)

Step 1: 48.5 g of isobornyl acrylate, 12 g of methyl acrylate, 0.6 g Trigonox 21, 115 g of isododecane; followed by addition, after reaction, of 60 g of isododecane.

Step 2: 182 g of methyl acrylate, 1.82 g of Trigonox 21S, 182 g of isododecane. After reaction, addition of 60 g of isododecane and evaporation to obtain a solids content of 31% by weight.

A dispersion in isododecane of polymethyl acrylate particles stabilized with an isobornyl acrylate/methyl acrylate (80/20) statistical copolymer stabilizer was obtained.

EXAMPLE 10 (OUTSIDE THE INVENTION)

Step 1: 48.5 g of isobornyl acrylate, 21 g of methyl acrylate, 0.7 g Trigonox 21, 130 g of isododecane; followed by addition, after reaction, of 65 g of isododecane.

Step 2: 173 g of methyl acrylate, 1.73 g of Trigonox 21S, 173 g of isododecane. After reaction, addition of 65 g of isododecane and evaporation to obtain a solids content of 31% by weight.

A dispersion in isododecane of polymethyl acrylate particles stabilized with an isobornyl acrylate/methyl acrylate (70/30) statistical copolymer stabilizer was obtained.

The stability 12 hours after the end of synthesis of the oily dispersions of polymethyl acrylate of Examples 1 and 7 to 10 was compared, and the following results were obtained.

| Example | Stabilizer | Stability |
|---|---|---|
| 1 | 92 isobornyl acrylate/8 methyl acrylate | Stable |
| 7 | 100 isobornyl acrylate | Stable |
| 8 | 85 isobornyl acrylate/15 methyl acrylate | Stable |
| 9 | 80 isobornyl acrylate/20 methyl acrylate | Phase separation and setting to a solid |
| 10 | 70 isobornyl acrylate/30 methyl acrylate | Phase separation and setting to a solid |

The results obtained show that the dispersions of polymethyl acrylate in isododecane are stable when the stabilizer is an isobornyl acrylate homopolymer or an isobornyl acrylate/methyl acrylate copolymer with an isobornyl acrylate/methyl acrylate weight ratio>80/20.

Moreover, the film obtained with the oily dispersions of Examples 7 and 8 have the following properties:

| Gloss at 20° | Resistance to fatty substances | Tacky |
|---|---|---|
| 72 | Resistant to fatty substances | Non-tacky |
| 69 | Resistant to fatty substances | Non-tacky |
| 65 | Resistant to fatty substances | Non-tacky |

EXAMPLES 11 AND 12 (OUTSIDE THE INVENTION)

Tests were performed with other monomers bearing a cyclic group by replacing the isobornyl acrylate, performing step 1 of Example 1, i.e. preparing a cyclic monomer/methyl acrylate (92/8) statistical copolymer stabilizer. All the stabilizers prepared in isododecane led to a medium that set to a solid in the form of a viscous precipitate. This shows that such stabilizers are unsuitable for forming an oily dispersion since they are incompatible with isododecane, in contrast with the stabilizers prepared in Examples 1 to 8 described previously.

| Examples | Stabilizer | Compatibility in isododecane |
|---|---|---|
| 11 | Cyclohexyl acrylate/methyl acrylate (92/8) | Incompatible (viscous precipitate) |
| 12 | Cyclohexyl methacrylate/methyl acrylate (92/8) | Incompatible (viscous precipitate) |

EXAMPLE 13

| | |
|---|---|
| Polymer dispersion of Example 1 | 96% |
| Tri-n-butyl citrate | 4% |

The film obtained after application to a contrast card and drying for 24 hours at 25° C. and 45% relative humidity has good tensile strength. The film is also glossy, resistant to olive oil and non-tacky.

EXAMPLE 14

| | |
|---|---|
| Polymer dispersion of Example 1 | 96% |
| Tripropylene glycol monomethyl ether | 4% |

The film obtained after application to a contrast card and drying for 24 hours at 25° C. and 45% relative humidity has good tensile strength. The film is also glossy, resistant to olive oil and non-tacky.

EXAMPLE 15

| | |
|---|---|
| Polymer dispersion of Example 1 | 96% |
| Trimethyl pentaphenyl trisiloxane (Dow Corning PH-1555 HRI Cosmetic Fluid from Dow Corning) | 4% |

The film obtained after application to a contrast card and drying for 24 hours at 25° C. and 45% relative humidity has good tensile strength. The film is also glossy, resistant to olive oil and non-tacky.

EXAMPLE 16

A skin makeup composition comprising the ingredients below is prepared:

| | |
|---|---|
| Polymer dispersion of Example 1 | 91.2% |
| Tripropylene glycol monomethyl ether | 3.8% |
| Iron oxides | 5% |

The composition applied to the skin makes it possible to obtain a glossy makeup film that is resistant to oils and non-tacky.

The polymer dispersion of Example 1 may be replaced with the dispersions of Examples 2 to 8.

EXAMPLE 17

A lip makeup composition comprising the ingredients below is prepared:

| | |
|---|---|
| Polymer dispersion of Example 1 | 91.2% |
| Trimethyl pentaphenyl trisiloxane | 3.8% |
| Isononyl isononanoate | 5% |
| Red 7 | 1% |

The composition applied to the lips makes it possible to obtain a glossy makeup film that is resistant to oils and non-tacky.

The polymer dispersion of Example 1 may be replaced with the dispersions of Examples 2 to 8.

EXAMPLE 18

An eyelash makeup composition comprising the ingredients below is prepared:

| | |
|---|---|
| Polymer dispersion of Example 1 | 57.6% |
| Tri-n-butyl citrate | 2.4% |
| Isododecane | 20% |
| Black iron oxides | 20% |

The composition applied to the eyelashes makes it possible to obtain a glossy makeup film that is resistant to oils and non-tacky.

The polymer dispersion of Example 1 may be replaced with the dispersions of Examples 2 to 8.

The invention claimed is:

1. A dispersion of particles of at least one polymer that is surface-stabilized with a stabilizer in a non-aqueous medium containing at least one apolar hydrocarbon-based oil containing from 8 to 16 carbon atoms, the polymer of the particles comprising a C1-C4 alkyl (meth)acrylate monomer; the stabilizer being an isobornyl (meth)acrylate polymer chosen from isobornyl (meth)acrylate homopolymer and statistical copolymers of isobornyl (meth)acrylate and of C1-C4 alkyl (meth)acrylate present in an isobornyl (meth) acrylate/C1-C4 alkyl (meth)acrylate weight ratio of greater than 4; wherein the polymer of the particles is present in a content ranging from 21% to 58.5% by weight relative to the total weight of the dispersion; and the amount of the stabilizer is from 15% to 30% by weight based upon the total weight of monomers of the stabilizer and particles of the at least one polymer and wherein the particles of the at least one polymer have an average size ranging from 50 to 500 nm.

2. The dispersion according to claim 1, wherein the polymer of the particles is a methyl acrylate and/or ethyl acrylate polymer.

3. The dispersion according to claim 1, wherein the polymer of the particles further comprises an ethylenically unsaturated acid monomer or the anhydride thereof.

4. The dispersion according to claim 1, wherein the polymer of the particles comprises from 80% to 100% by weight of a C1-C4 alkyl (meth)acrylate and from 0 to 20% by weight of an ethylenically unsaturated acid monomer, relative to the total weight of the polymer.

5. The dispersion according to claim 1, wherein the polymer of the particles is chosen from:
methyl acrylate homopolymers
ethyl acrylate homopolymers
methyl acrylate/ethyl acrylate copolymers
methyl acrylate/ethyl acrylate/acrylic acid copolymers
methyl acrylate/ethyl acrylate/maleic anhydride copolymers
methyl acrylate/acrylic acid copolymers
ethyl acrylate/acrylic acid copolymers
methyl acrylate/maleic anhydride copolymers and
ethyl acrylate/maleic anhydride copolymers.

6. The dispersion according to claim 1, wherein the stabilizer is a statistical copolymer of isobornyl (meth) acrylate and of C1-C4 alkyl (meth)acrylate present in an isobornyl (meth)acrylate/C1-C4 alkyl (meth)acrylate weight ratio greater than or equal to 5.

7. The dispersion according to claim 1, wherein the stabilizer is chosen from:
isobornyl acrylate homopolymers
statistical copolymers of isobornyl acrylate/methyl acrylate
statistical copolymers of isobornyl acrylate/methyl acrylate/ethyl acrylate and
statistical copolymers of isobornyl methacrylate/methyl acrylate.

8. The dispersion according to claim 1, wherein the combination of the stabilizer and polymer of the particles present in the dispersion comprises from 10% to 50% by weight of polymerized isobornyl (meth)acrylate and from 50% to 90% by weight of polymerized C1-C4 alkyl (meth) acrylate, relative to the total weight of the combination of the stabilizer and polymer of the particles.

9. The dispersion according to claim 1, wherein the hydrocarbon-based oil is isododecane.

10. The dispersion according to claim 1, which comprises from 30% to 65% by weight of solids, relative to the total weight of the dispersion.

11. The dispersion according to claim 1, which comprises a plasticizer chosen from tri-n-butyl citrate, tripropylene glycol monomethyl ether and trimethyl pentaphenyl trisiloxane.

12. A composition comprising, in a physiologically acceptable medium, a polymer dispersion according to claim 1.

13. The composition according to claim 12, which comprises a cosmetic additive chosen from water, fragrances, preserving agents, fillers, dyestuffs, UV-screening agents, oils, waxes, surfactants, moisturizers, vitamins, ceramides, antioxidants, free-radical scavengers, polymers and thickeners.

14. A non-therapeutic cosmetic process for treating keratin materials, comprising the application to the keratin materials of a composition according to claim 13.

15. The dispersion according to claim 1, wherein the polymer of the particles comprises an ethylenically unsaturated acid monomer or the anhydride thereof chosen from (meth)acrylic acid, maleic acid and maleic anhydride.

16. The dispersion according to claim 2, wherein the polymer of the particles comprises an ethylenically unsaturated acid monomer or the anhydride thereof chosen from (meth)acrylic acid, maleic acid and maleic anhydride.

17. The dispersion according to claim 1, wherein the polymer of the particles comprises from 80% to 100% by weight of C1-C4 alkyl (meth)acrylate and from 0 to 20% by weight of ethylenically unsaturated acid monomer, relative to the total weight of the polymer.

18. The dispersion according to claim 1, wherein the polymer of the particles is present in a content ranging from 36% to 42% by weight relative to the total weight of the dispersion.

* * * * *